(12) United States Patent
Perkins (10) Patent No.: US 8,075,632 B2
(45) Date of Patent: Dec. 13, 2011

(54) TRANSTIBIAL SOCKET FOR EXTERNAL PROSTHESIS

(75) Inventor: Dale Perkins, Boise, ID (US)

(73) Assignee: Coyote Design & Manufacturing, Inc., Boise, ID (US)

( * ) Notice: Subject to any disclaimer, the term of this patent is extended or adjusted under 35 U.S.C. 154(b) by 986 days.

(21) Appl. No.: 11/949,018

(22) Filed: Nov. 30, 2007

(65) Prior Publication Data

US 2008/0161939 A1  Jul. 3, 2008

Related U.S. Application Data

(60) Provisional application No. 60/872,287, filed on Nov. 30, 2006.

(51) Int. Cl.
*A61F 2/80* (2006.01)
(52) U.S. Cl. .......................................... 623/34
(58) Field of Classification Search ............... 623/27–37
See application file for complete search history.

(56) References Cited

U.S. PATENT DOCUMENTS

| 6,334,876 | B1 | 1/2002 | Perkins | |
| 2005/0278039 | A1* | 12/2005 | Nobbe | 623/31 |

OTHER PUBLICATIONS

Picken, Robert R., "The Below-Knee Prosthesis," Lower Extremity Amputation, Second Edition,1992, pp. 31-32, Rehabilitation Institute of Chicago, USA.
"Chapter 4:Components," Orthotics Prosthetics Program, 1998, pp. 4 1-4, University of Texas Health Science Center of Dallas, USA.
Excerpt from:Lower limb Prosthetics Manual,1982 Revision, pp. 107, 113-114, 119-120, S73, S79, New York University Medical Center, USA.

* cited by examiner

*Primary Examiner* — Bruce E Snow
(74) *Attorney, Agent, or Firm* — Pedersen and Company, PLLC; Ken J. Pedersen; Barbara S. Pedersen (57) ABSTRACT

A prosthetic hard socket has a modified curvature and/or shape, which eliminates or de-emphasizes the patellar bar to eliminate or reduce pressure on the wearer's patellar tendon, and, instead, enhances support of the anterior tibial condyle and/or tibial tubercle. Thus, the preferred socket is designed with the patellar tendon preferably not being weight-bearing. The preferred curvature and/or shape comprises a lowered socket edge and/or a gap in the socket wall in the region of the patellar tendon, so that the hard structure of the socket does not directly support or press upon the patellar tendon. The invented socket may include inwardly-protruding regions on each side of the lowered edge/gap, for helping to "capture" or otherwise press on a portion of the tibia for improved rotational control. This combination of shapes and curvatures provides for improved rotational control, comfort, and range of motion including even full extension or hyperextension. A flexible and/or cushioning member may be placed in the gap/trough (that is caused by the lowered edge or removed wall portion), for example, a fabric, leather, rubber, or other member may be attached to the socket to across a V-shaped trough of the lowered edge of the hard socket.

17 Claims, 10 Drawing Sheets

Prior Art

TRANSTIBIAL SOCKET FOR EXTERNAL PROSTHESIS

This application claims priority of Provisional Application 60/872,287, filed Nov. 30, 2006, the entire disclosure of which is incorporated herein by this reference.

BACKGROUND OF THE INVENTION

1. Field of the Invention

This invention relates to the field of lower limb external prosthetics, specifically below-the-knee amputations, such as transtibial and Symes amputations. The invention relates to prosthetics sockets that provide enhanced comfort and control without providing a patellar tendon bar.

2. Related Art

Conventional hard sockets for lower limb external prosthetics, for example, those portrayed in FIGS. 1-5, comprise a patellar-tendon-bar. It should be noted that the patellar-tendon bar (B) may be located at various levels (vertical distances along the socket), depending upon the height and shape of the socket, which in turn is substantially determined by the length and shape of the residual limb. The conventional patellar bars (B) of the prior art sockets in FIGS. 1A and B are located a significant way down the socket from the top edge of the socket, for example, several inches down from the top edge. On the other hand, the conventional patellar bar (B) of FIGS. 2-5 is near the top edge of the socket (formed by approximately the top two inches of the socket in that area).

The patellar-tendon-bar or "patellar bar," provided in prosthetic "hard sockets" for transtibial or "Symes" amputations, is an inwardly-protruding portion of the socket that contacts and supports the patellar-tendon of the residual limb. This inwardly-protruding portion, though it is traditionally called a "bar" by those of skill in this art, is not literally what most readers would think of as a bar, in that it is not a separate, elongated member installed or imbedded into the socket material. Rather, the bar is a curvature of the socket wall inward into the interior space of the socket in such a location that the wearer's patellar tendon rests on and is supported by the curved socket surface.

While the bar's support of, and impingement against, the patellar tendon in prior art sockets is intended to provide non-bone contact point and support, the inventor believes that this type of support actually leads to discomfort, lack of rotational control, and reduced range of motion. The inventor believes that this type of prior-art support of the weight of the wearer interferes with the tendon during movement in a way that prevents full extension and proper flexion.

The prior art sockets, and also the improved sockets of the invention, may be worn with roll-on liners, including the modern, preferred, roll-on liner with an inner layer of "gel" or other rubbery material and an outer layer of fabric, textile, or other woven material. The preferred embodiments of the invented socket may incorporate various devices for assisting in connecting or holding the socket on the residual limb. For example, a distal lock may be included for anchoring the socket to the roll-on liner, such as are known by those of skill in this field.

SUMMARY OF THE INVENTION

The invention comprises a socket with a modified curvature and/or shape, which eliminates or de-emphasizes the patellar bar to eliminate or reduce pressure on the patellar tendon, and, instead, enhances support of the anterior tibial condyle and/or tibial tubercle. The preferred curvature and/or shape comprises a lowered socket edge in the region of the user's patellar tendon, so that the hard structure of the socket does not directly support or impinge upon the patellar tendon. The invented socket may include indentations on each side of the lowered edge, thus, on each side of and substantially out of the way of the patellar tendon, for helping to "capture" a portion of the tibia for improved rotational control. This combination of shapes and curvatures provides for improved rotational control, comfort, and range of motion.

In the preferred embodiment, the conventional patellar bar is eliminated, and the upper edge of the hard wall of the socket is preferably lowered relative to where it would be if the hard wall were intended to contact/support the patellar tendon region of the residual limb. A strap, patch, cloth, or other member may be placed at the "trough" or "notch" of the lowered, typically downwardly-curving edge of the socket. Preferably, this member is somewhat flexible, somewhat elastic, and/or otherwise forgiving, while also giving some degree of containment of the portion of the liner-covered residual limb that contacts said member. A very flexible and/or cushioning member (such as a rubber or fabric sheet) may be placed in this position for less aggressive walkers, or a somewhat flexible but more rigid and inelastic member (such as leather) may be placed in this position for a more aggressive walker. Or, the member may be entirely eliminated, depending on the comfort, control, and containment needs of the user, so that there is no socket portion or other structure supporting or contacting the liner-covered residual limb in the area of the patellar tendon. Thus, this region of the socket may be customized to the walker, while giving increased range of motion compared to conventional sockets for transtibial/Symes amputees.

DESCRIPTION OF THE PREFERRED EMBODIMENTS

Referring to FIGS. 1A-D, and 2-5, one may see examples of prior art sockets with embodiments of tendon-support hard socket wall ledges or inward-curvature, called "patellar bars" as discussed above. Referring to FIGS. 2-5, socket 10 has a top edge 12 and, near the top edge, is the concave (from the outside) bar B. As discussed above, the bar B need not always be so close to the top edge 12, as illustrated in FIGS. 1A-D. Also, there may be ways of making a prior art patellar bar, other than curvature of the socket wall, for example, placement or molding of additional material at the inner wall of the socket to provide said "ledge" against which the patellar tendon rests/pushes.

The bar B provides a substantially-horizontal "shelf" 15 on the inside of the socket against which the patellar tendon is placed. One may see, especially in FIGS. 2 and 3, that the top edge in the region of the prior art bar B (that is near the top edge TE) is typically a gentle, large-radiused edge, that is, preferably a wide U-shape, but not a V-shape. In embodiments wherein the patellar bar B is lower down on the socket relative to the top edge (FIGS. 1A-D), the socket wall above the bar B typically continues up and over the region of the knee cap, extending continuously and generally vertically up to a top edge TE; in such embodiments, the top edge is also typically a wide U-shape or horizontally straight, but is not a V-shape.

Figure 1A:
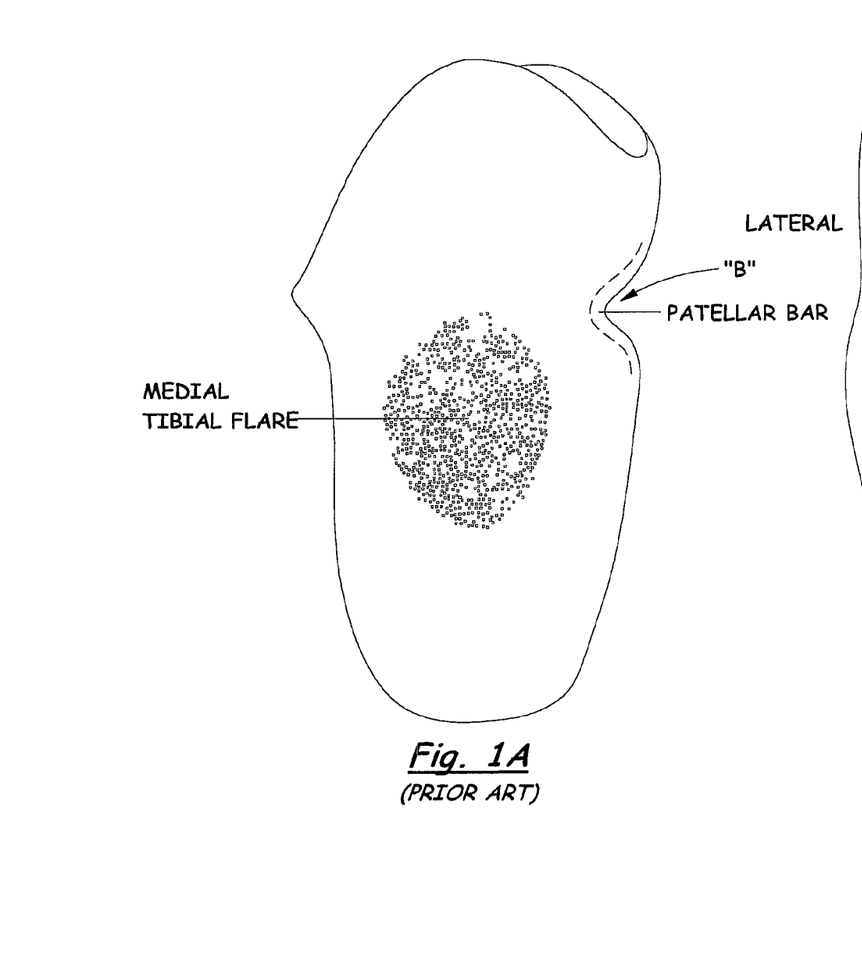
FIGS. 1A and 1B are a side view and a rear view, respectively, of a prior art hard socket comprising a conventional patellar bar B.
Figure 1B:
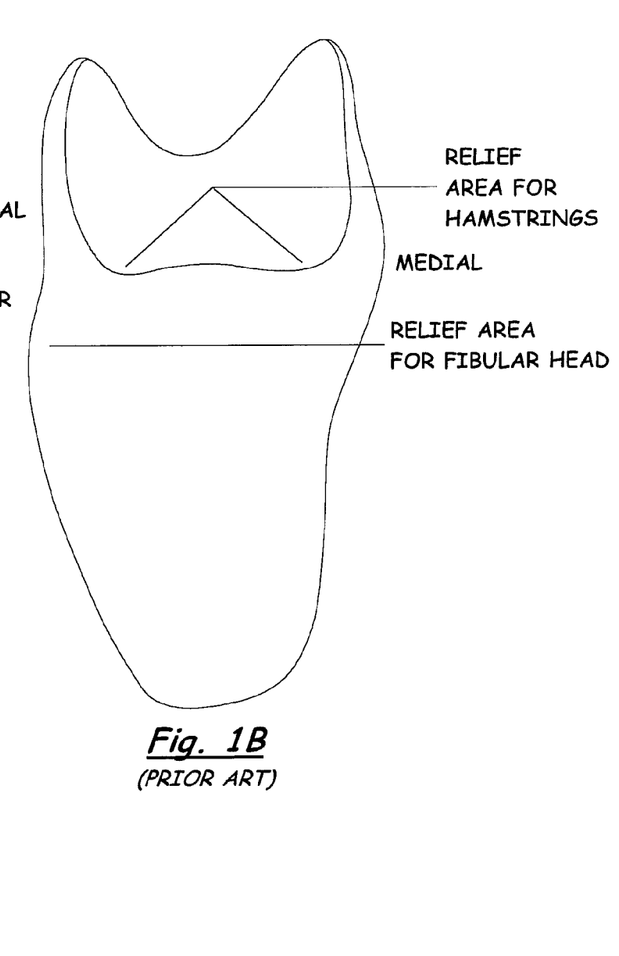
Figure 1C:
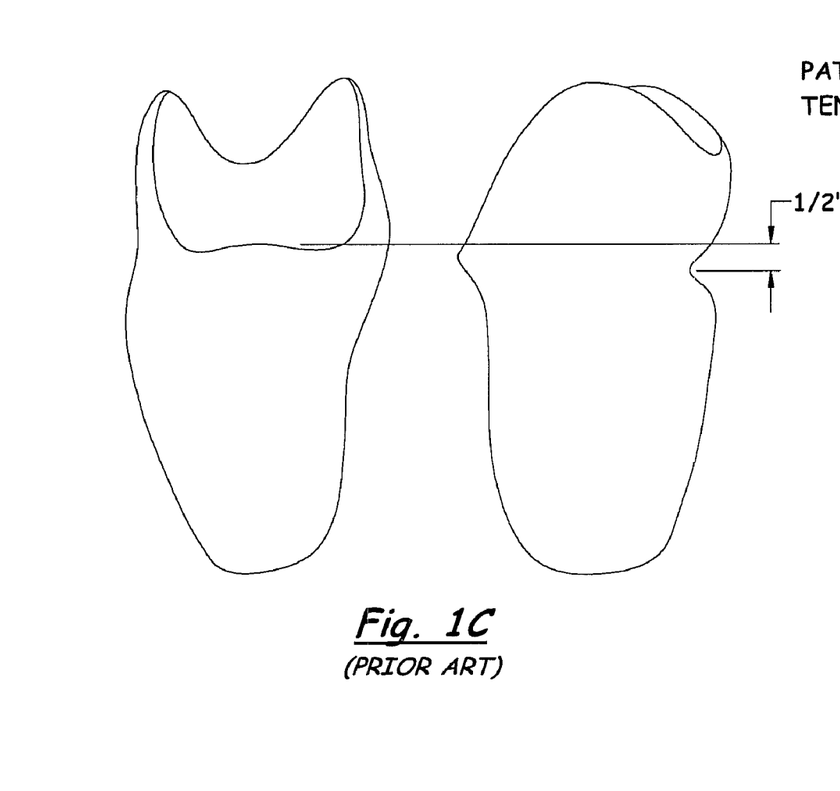
FIG. 1C is a comparison of the side and rear views of FIGS. 1A and 1B, illustrating the typically placement of the patellar tendon bar.
Figure 1D:
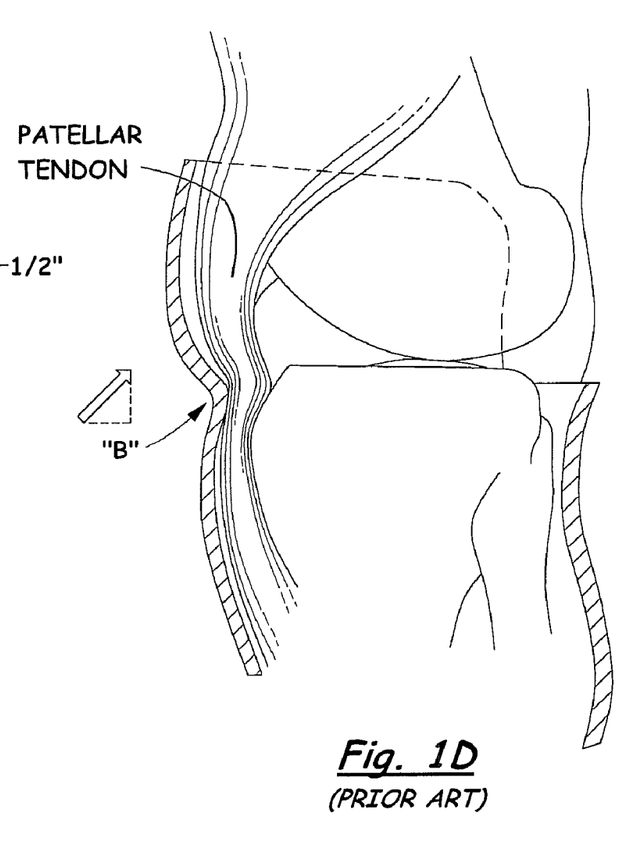
FIG. 1D is a side view of another prior art hard socket, wherein the patellar tendon and the residual limb bone structure are portrayed, along with the typically direction of force against the tendon is portrayed.
Figure 2:
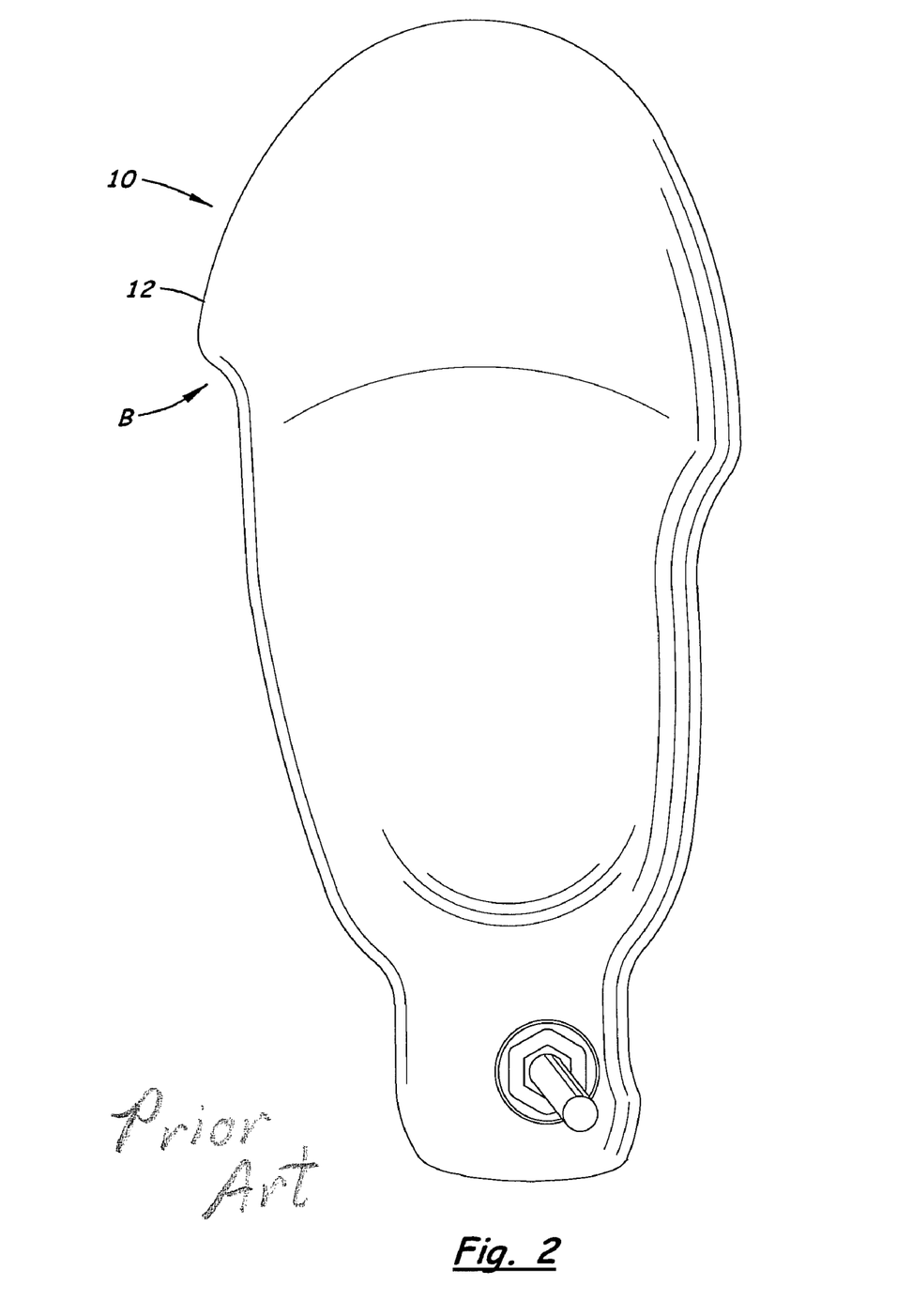
FIG. 2 is a side view of a prior art socket with a patellar bar (B). The curvature of the hard socket wall that forms the prior art patellar bar is a concave area (viewed from the outside) and a convex area (viewed from the inside of the interior socket space S), wherein the socket wall protrudes into the interior space of the hard socket to form a ledge or other hard, horizontal support structure on which rests the patellar tendon, and against which said patellar pushes during walking.
Figure 3:
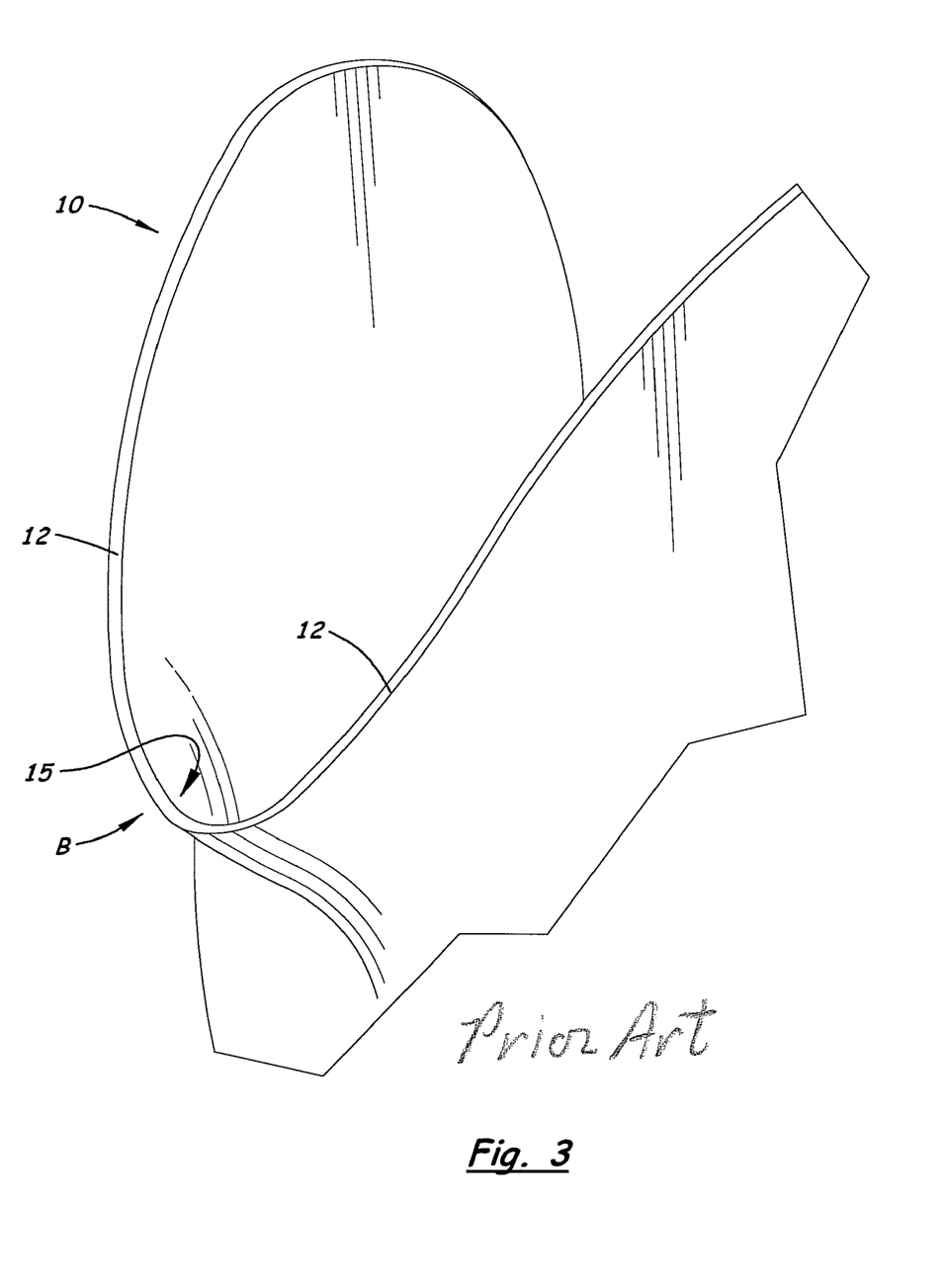
FIG. 3 is partial, front, close-up view of the patellar bar region of the prior art hard socket of FIG. 2.
Figure 4:
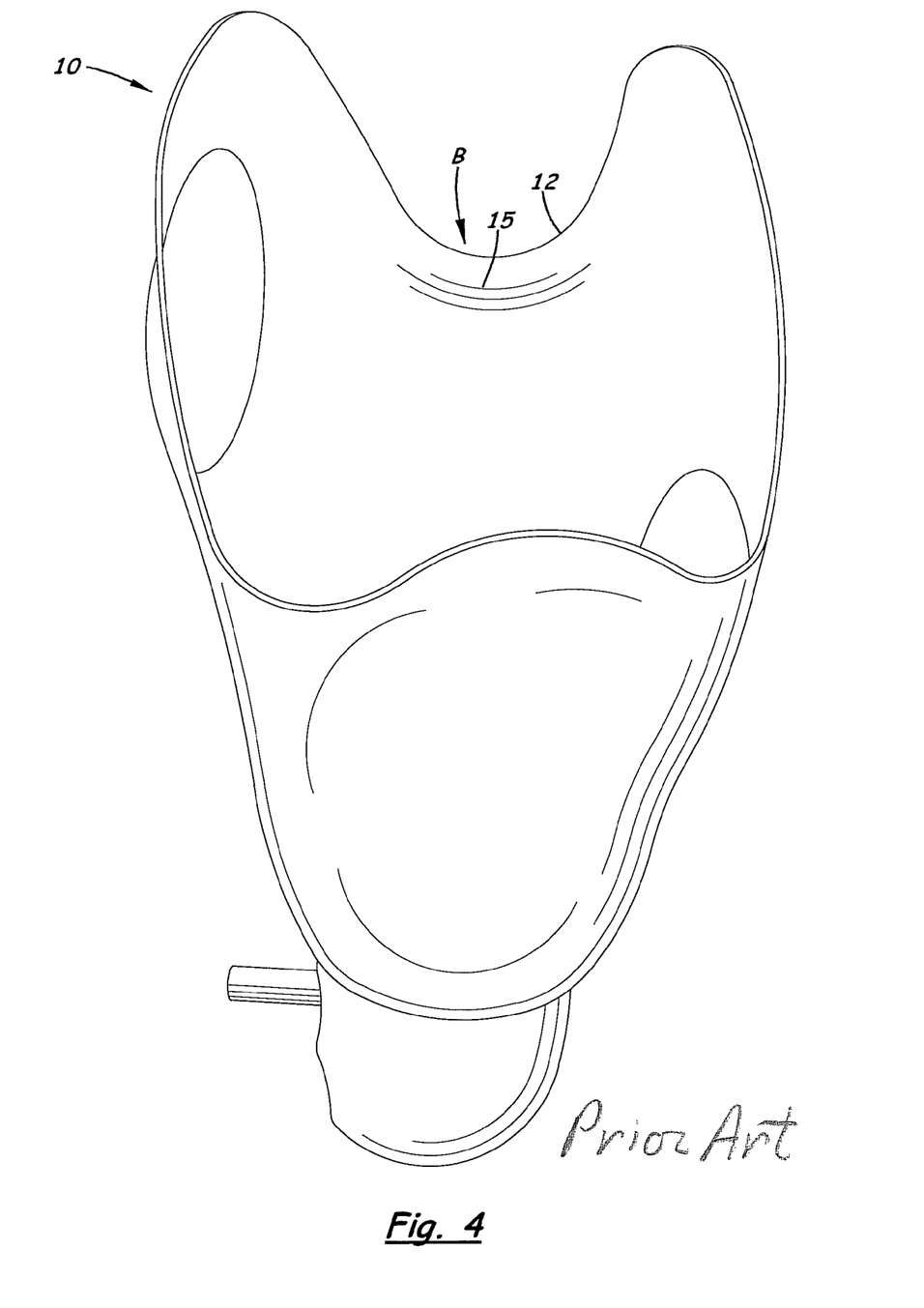
FIG. 4 is rear view of the prior art hard socket of FIGS. 2 and 3.
Figure 5:
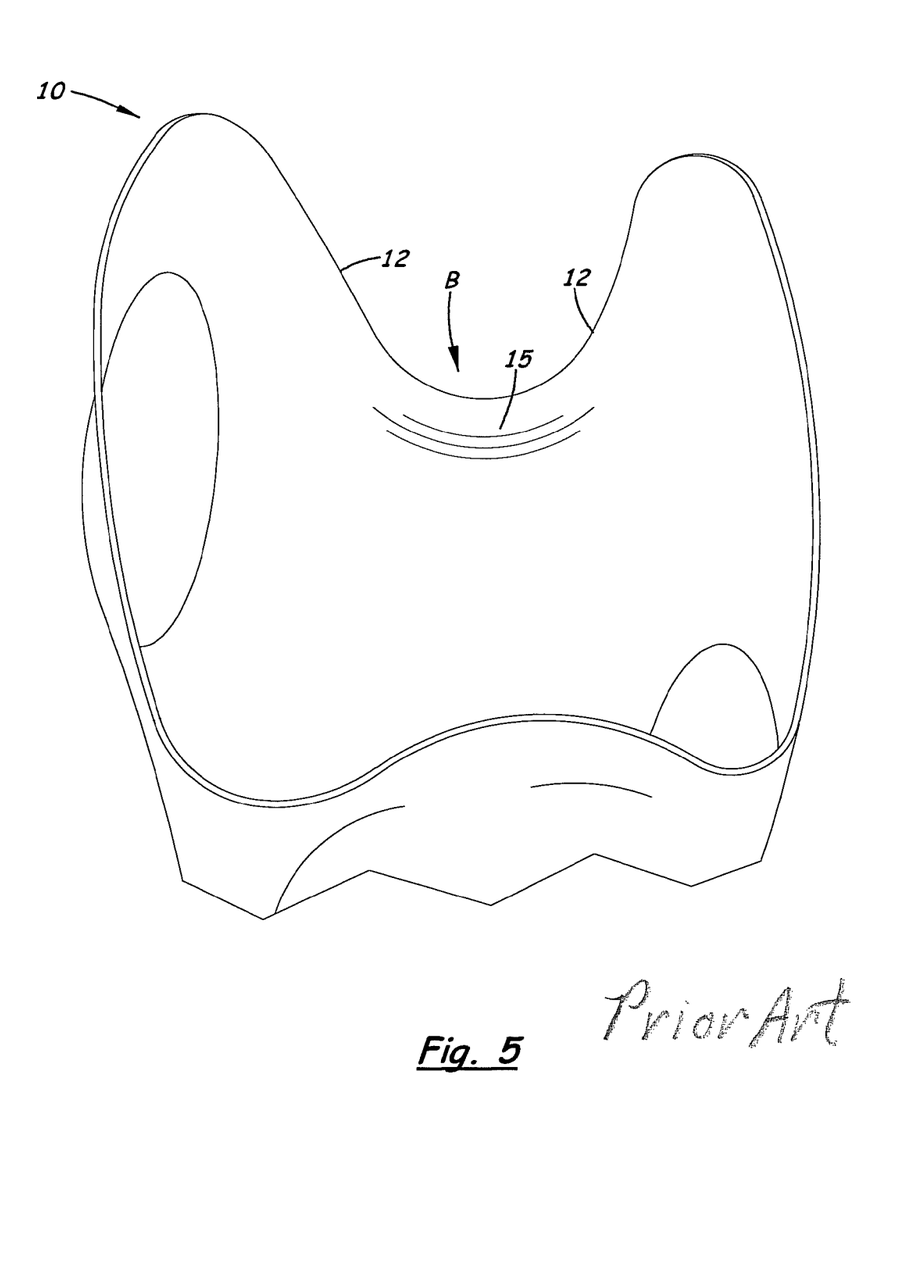
FIG. 5 is a rear, close-up view of the upper portion of the prior art socket of FIGS. 2-4.
Figure 6:
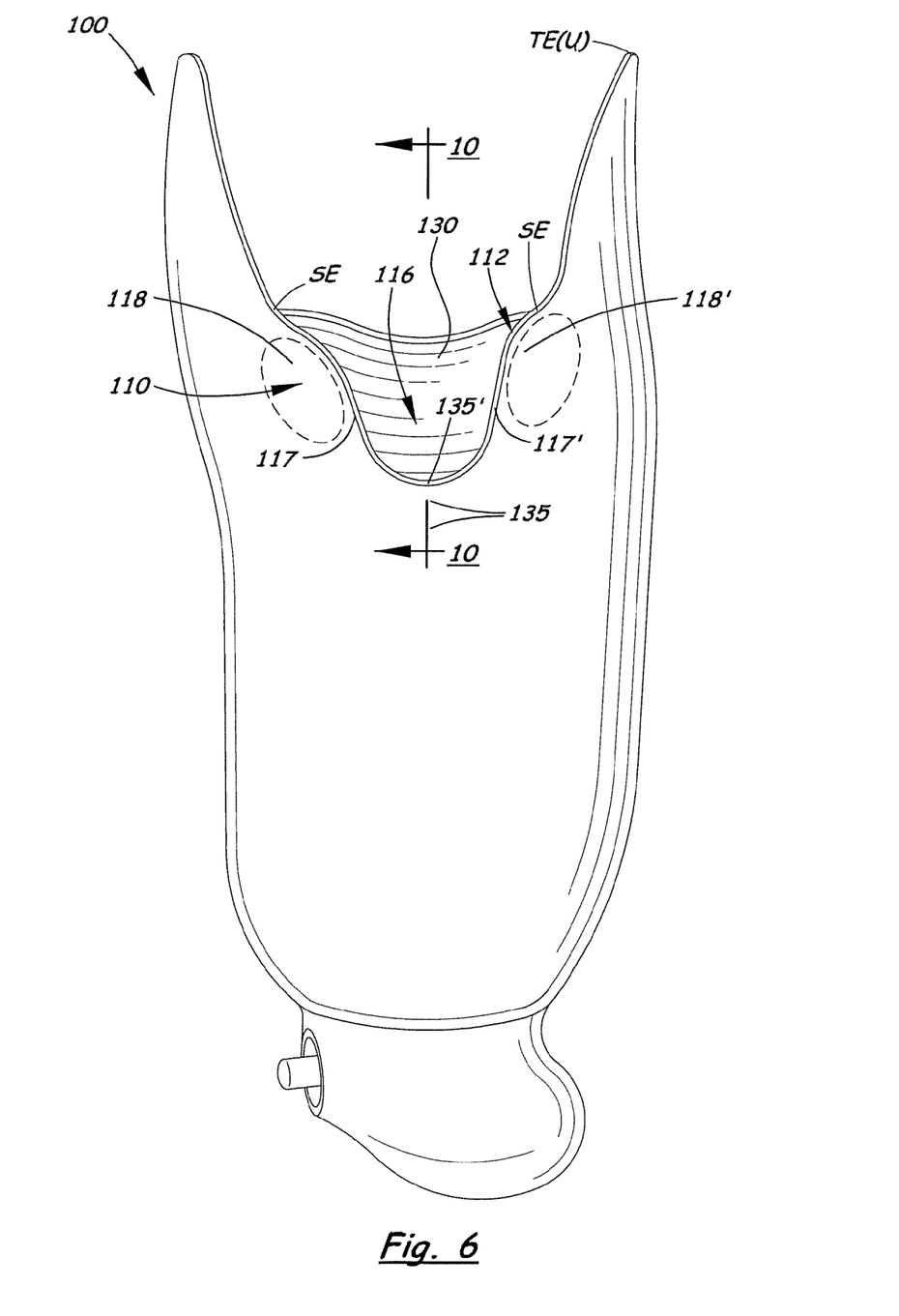
FIG. 6 is a front view of one embodiment of the invented hard socket for a below-the-knee prosthesis.
Figure 7:
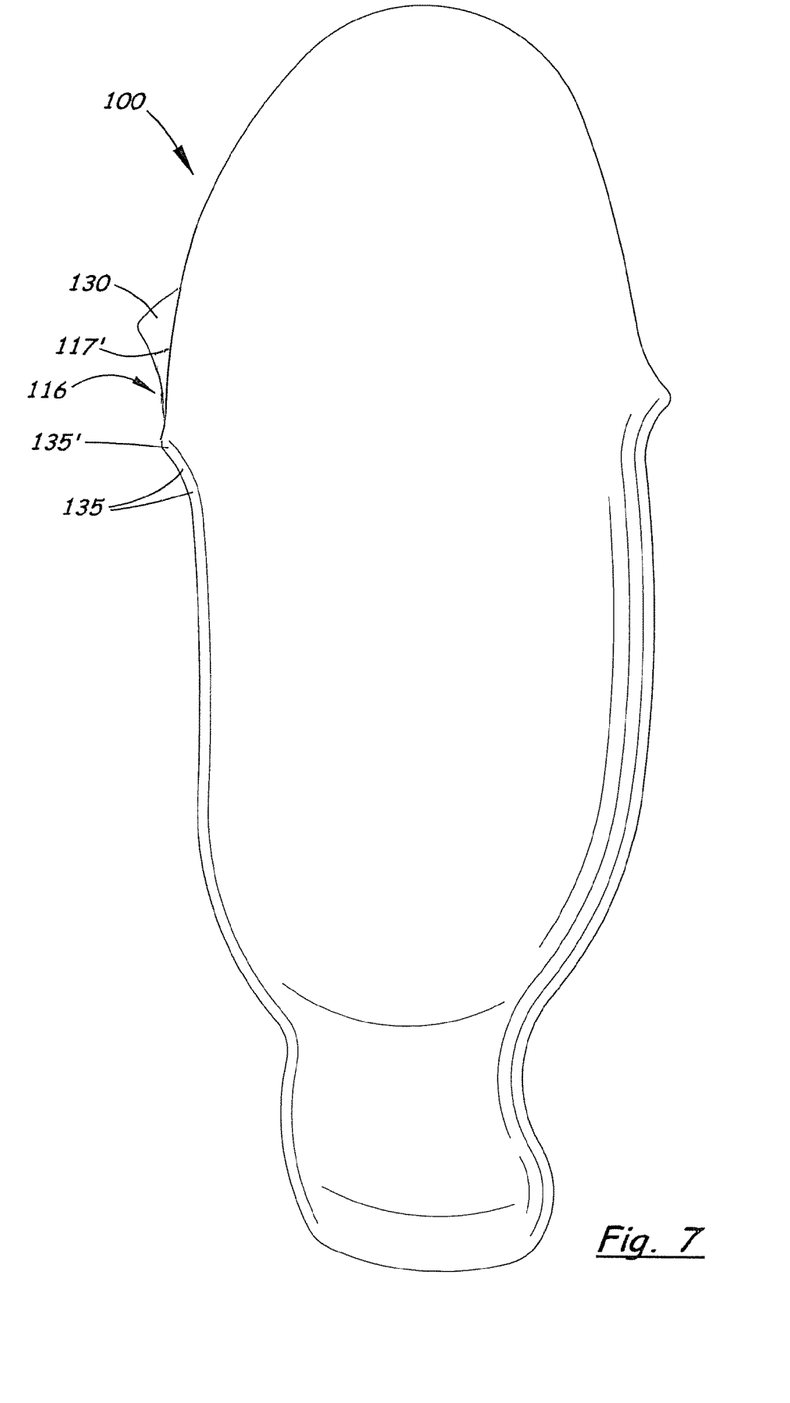
FIG. 7 is side view of the embodiment of FIG. 6.
Figure 8:
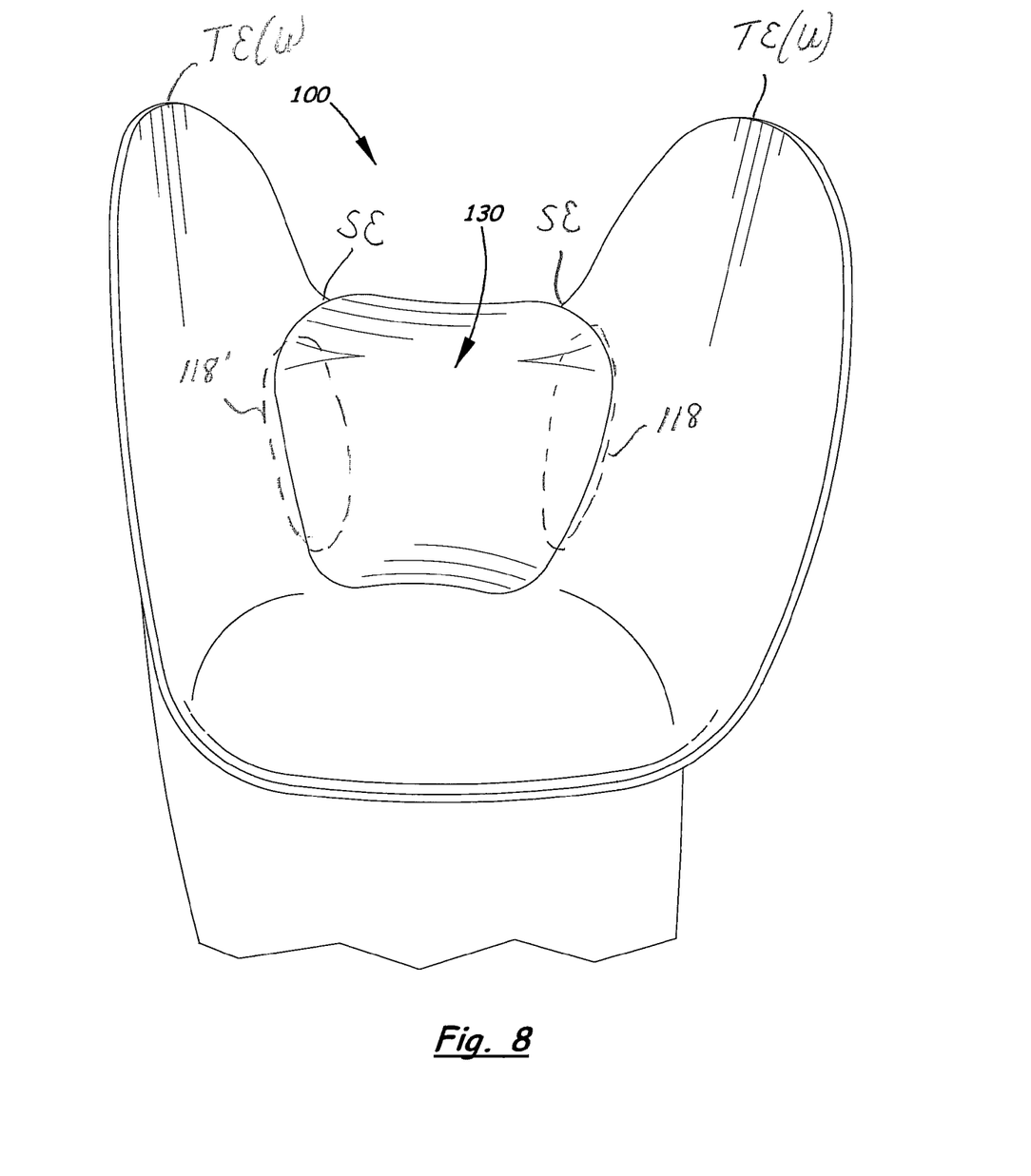
FIG. 8 is a partial, rear view of the upper portion of the embodiment of FIGS. 6 and 7.

In contrast, one may see one embodiment of the invented socket 100 and the invented tibia support system 110 (as opposed to a patellar tendon support system). Socket 100 has an upper, front (anterior) edge 112 that is substantially "dipped," "lowered" or otherwise made into preferably a V-shaped notch or "trough" 116. This trough 116 is adapted to purposely keep the hard socket wall out of the way of the patellar tendon, with the top edge 112 notch sides 117, 117' extending generally vertically along each side of the patellar tendon not interfering with the tendon and preferably not contacting the portion of the liner-covered residual limb in which said tendon resides. The V-shaped trough 116 preferably has a slightly rounded bottom point wherein the sides 117, 117' meet, and is preferably about 2-4 inches deeper than the surrounding edges of the socket SE, and preferably about 4-6 inches deeper than the uppermost portions of the top edge TE(U). The V-shaped trough 116 is preferably about 2-3 inches wide from side 117 to side 117' at the middle level of the trough (at location where call-out lines for 117, 117' touch the trough sides).

Preferably, at each side of the trough 116 is a recessed portion 118, 118' of the socket wall (portrayed by dashed lines in FIGS. 6 and 8, said recessed portions 118, 118' (concave/recessed from an outside perspective in FIG. 6, and convex from an inside-the-socket perspective in FIG. 8) being adapted to press upon the residual limb (actually the liner-covered limb) on the sides of the anterior region of the tibia. The tibia is somewhat v-shaped near its anterior in transverse cross-section, allowing the preferred recessed portions 118, 118' to extend at least a small distance along the sides of the tibia to "capture" the anterior tibial condyle. This acts to at least somewhat "capture" the tibia and lend rotational control, in a way that has been found much more satisfactory in many embodiments compared to a prior art patellar bar style of socket.

The recessed portions 118, 118' may be made by pressing inward, or otherwise molding, convex surfaces on the inside wall of the socket. Alternatively, other methods, such as adding material or thickness in these areas (areas of 118, 118') may be effective. The recessed portions 118, 118' may be the same size, or different sizes, as desirable for fitting the wearer. During the molding process, the recessed portions 118, 118' may be formed, for example, by pressing inward on the socket to "fit" to the particular wearer's tibia.

Preferably, there is a containment member 130 provided in the space formed by the trough 116, such that the containment member extends across the trough 116 from edge 117 to edge 117'. This member 130 has at least some flexibility, cushioning, and/or resilience, at least to a greater degree that the socket wall. The member 130 may range from very flexible (such as cloth, elastic, thin rubber, closed cell foam, or various woven fabrics or stretchable material), to only somewhat flexible (such as leather or a firm rubber).

Member 130 preferably provides some containment of the residual limb (and the preferred liner that covers the limb), helps prevent wear of the liner and/or irritation of the limb by the trough edges, and may provide a small amount of control and support. Generally, the member fills the space near/against the patellar tendon region of the wearer's residual limb, and it is preferred that there is relatively little force placed upon the patellar tendon by this member, especially when compared to the force that would be applied by the hard wall of a conventional socket.

Figure 9A:
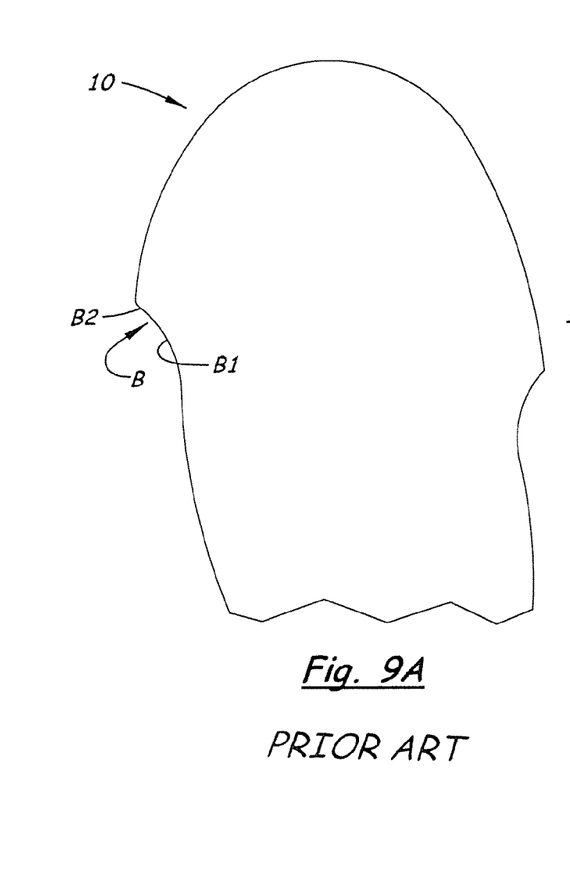
FIG. 9A is a partial side view of a prior art hard socket with a patellar bar (for comparison to the embodiment of the invention shown in FIGS. 9A and 10).
Figures 9B, 10:
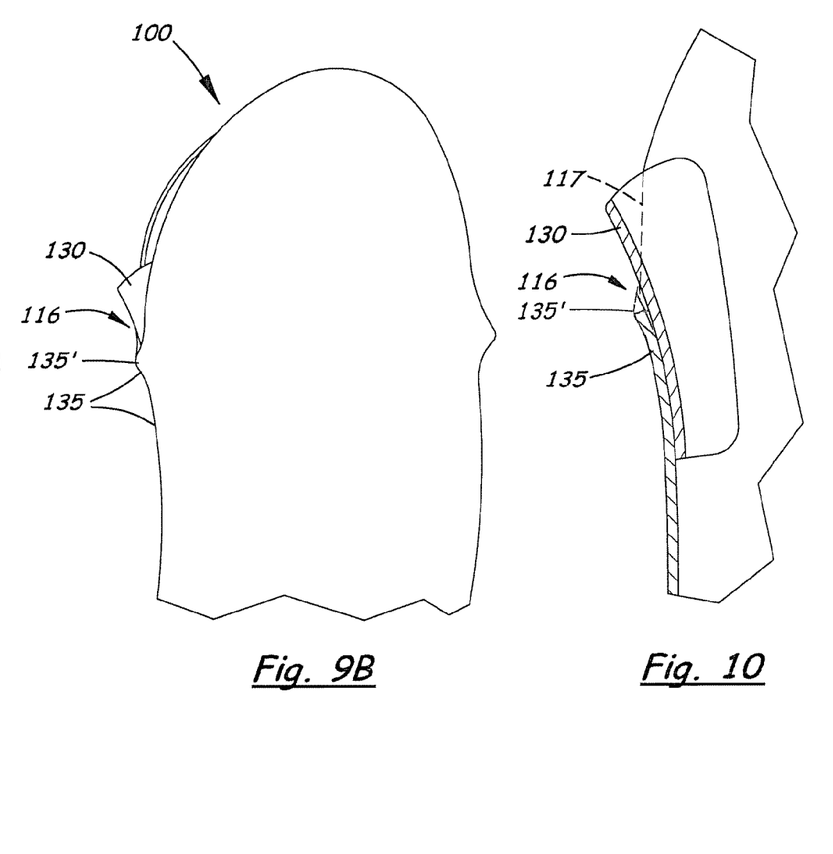
FIG. 9B is a partial side view of an upper portion of the embodiment of FIGS. 6-8.
FIG. 10 is a partial, close-up, cross-sectional view of the embodiment of FIGS. 6-8 and particularly the portion of the embodiment that is drawn in FIG. 9B.

Preferably, the containment member 130 is adhesively connected to the socket wall, or it could be molded-into the edge of the socket or otherwise bonded or attached, preferably without rigid or protruding fasteners. Preferably, there is preferably no protrusion, and especially no hard protrusion, on the inside surface of the member 130 or the socket wall near the tendon. If the member 130 is adhesively attached to the socket wall, it will preferably be attached to the inside wall so that pressure by the residual limb acts to press it out against the socket wall. There may be a seam/transition between edges of the member 130 and the socket wall, but, as the member 130 is preferably not very thick, said seam/transition should tend to be comfortable for the wearer. Preferably, the member 130 is connected to the hard socket wall on three edges (bottom and right and left side edges), but not on its top edge. Thus attached at three sides/edges, the member 130 will stay in place except for some stretching or bending outwardly, especially at and near the top, free edge, when pressure is applied by the residual limb FIGS. 9A and 9B compare the upper portions of a prior art socket 10 having a patellar tendon bar B with an embodiment of the invented socket 100 (both in side view), respectively. One may see, in the prior art socket, the relatively indented area B1 and the relatively protruding area B2, which, together, form the tendon bar B against which the wearer's patellar tendon will rest and push. In the prior art socket of FIG. 9A, one may imagine the knee of the wearer protruding out of the socket and to the left above the bar B, and the patellar tendon impinging against the bar B as it extends along and against both B1 and B2. In socket 100 of FIG. 9B, on the other hand, the anterior/front, upper portion of the socket is, in effect, cut away to form trough 116 and to remove all or most of area B1 and all of area B2, leaving a space or gap in its place. In the gap between the side edges of the trough (filled preferably only with the flexible and/or stretchable containment member), there is much more room for range of motion in the gait of the wearer.

Preferably, therefore, there is no inwardly-protruding shelf in the area of wall portion 135. In most embodiments, the wall portion 135, which is below the lowest part 135' of the trough, may curve outward a little or have a rounded edge, for comfort, but wall portion 135 is low enough that it does not press on the tendon. Instead of attempting support and control by means of the patellar tendon pressing on a horizontal ledge, the recessed portions 118, 118' may provide supportive and/or control surfaces against which the anterior tibial condyle and/or tibial tubercle may press.

It should be noted that, by removing a significant portion of the socket wall at the patellar tendon region to form the preferred trough 116 (or another shape of trough or gap in the socket wall) allows most wearers to comfortably and quite naturally walk uphill. The inventor believes that a major problem with the traditional socket having a patellar tendon bar, is that, during some portions of the wearer's gait, the tendon naturally moves outward relative to the rest of the residual limb. During these portions of the gait, therefore, the tendon pushes the socket to undesirable positions relative to the residual limb, creating gaps between the limb and the socket. This naturally makes difficult a good fit of a patellar-tendon-bar-type socket to the wearer, as the socket and tendon bar that fit during some parts of the gait do not fit at other times.

In some embodiments of the apparatus, the socket may be described as: An external below-the-knee prosthesis socket comprising:

a socket hard wall surrounding and defining a socket interior space and having an upper edge defining an opening for receiving a residual limb of a wearer into the socket interior space;

wherein said socket hard wall comprises a V-shaped notch in said upper edge, wherein the notch extends downwardly to provide a gap in the hard wall adapted to be located where a wearer's patellar tendon will reside when the residual limb is in the socket interior space; and a flexible member provided in said V-shaped notch and connected to said socket hard wall so that the flexible member extends across the notch for contacting the wearer's residual limb or liner-covered residual limb.

In most and preferably all embodiments, the flexible member does not encircle the residual limb. In most and preferably all embodiments, the flexible member does not extend underneath the distal end of the residual limb. In many embodiments, the flexible member is glued to the hard socket. The flexible member may be a patch of flexible fabric. In order to enhance rotation control, the preferred hard wall comprises two recesses that extend inward into the interior space of the socket on each of two sides of said V-shaped notch, for pressing against the wearer's anterior tibial condyle. One may see from the detailed description that the hard wall of the socket preferably comprises no patellar bar for pressing against the wearer's patellar tendon.

In some embodiments, the socket may be described as: a rigid socket wall surrounding and defining a socket interior space and having a top edge defining an opening for receiving a residual limb of a wearer into the socket interior space;

wherein the top edge has an uppermost portion and a lowermost edge portion and said lowermost portion is a V-shaped notch that extends generally vertically downward a distance of 4-6 inches below said uppermost portion of the top edge, wherein said notch provides a gap in the rigid socket wall that is adapted to be located where a wearer's patellar tendon will reside when the residual limb is in the socket interior space; and a non-rigid member provided in said V-shaped notch and connected to said rigid wall so that the non-rigid member extends across said gap for contacting the wearer's residual limb or liner-covered residual limb, and wherein said non-rigid member does not extend upward as high as said uppermost portion of the top edge. Preferably, the non-rigid member is not a strap or other member that encircles the residual limb or any part of the body, and preferably does not extend underneath the distal end of the limb. The non-rigid member may be glued of otherwise bonded to the hard socket. The non-rigid member may be a patch selected from the group consisting of: fabric, rubber, and leather. The rigid socket wall may have an interior surface that further comprises two convex portions that protrude into the socket interior space on each of two sides of said V-shaped notch, for pressing against the wearer's anterior tibial condyle. The preferred rigid socket wall comprises no patellar bar for pressing against the wearer's patellar tendon and preferably no structure that could be reasonably described as a horizontal internal wall ridge for pressing on said tendon.

The invention may also comprises methods of making and using a prosthesis socket. For example, a method of making a below-the-knee prosthesis socket is presented, the method comprising:

forming a hard socket wall having a top edge, the top edge having a V-shaped notch extending axially downward to provide a gap in the socket wall into which a wearer's patellar tendon resides when the wearer's residual limb is in said socket; so that no portion of the hard socket wall presses against the patellar tendon during use of the socket.

The method may comprise providing a flexible patch across the V-shaped notch and generally parallel to the hard socket wall, so that said flexible patch contact the wearer's liner-covered residual limb at the patellar tendon. The method may comprise forming indentations in the hard socket wall on each of two sides of the V-shaped notch, wherein said indentations protrude into the interior space of the socket to press against the wearer's anterior tibial condyle. Preferably, the socket has no patellar tendon bar, and no horizontal ledge in the interior surface of the hard socket wall at the patellar tendon region of the residual limb.

A method is provided of making a hard socket for a below-the-knee external prosthesis, the method comprising forming a hard socket that surrounds and defines a well for receiving a wearer's residual limb wherein the hard socket is formed with a gap or space in the wall of the hard socket in an upper front region of the hard socket, wherein said gap or space extends axially downward toward a distal end of the socket 4-6 inches to open the wall in the region of the patellar tendon of a wearer so that the wall does not press upon the patellar tendon. A flexible panel may be provided in the gap or space and generally parallel to the wall near said gap or space, said flexible panel flexing during gait of a wearer as the patellar tendon moves outward during portions of the gait.

Although this invention has been described above with reference to particular means, materials and embodiments, it is to be understood that the invention is not limited to these disclosed particulars, but extends instead to all equivalents within the broad scope of the following claims.

I claim:

1. An external below-the-knee prosthesis socket comprising: a socket hard wall surrounding and defining a socket interior space and having an upper edge defining an opening for receiving a residual limb of a wearer into the socket interior space; wherein said socket hard wall comprises a V-shaped notch in said upper edge, wherein the notch extends downwardly to provide a gap in the hard wall adapted to be located where a wearer's patellar tendon will reside when the residual limb is in the socket interior space; and a flexible member provided in said V-shaped notch and connected to said socket hard wall so that the flexible member extends across the notch for contacting the wearer's residual limb or liner-covered residual limb, wherein the flexible member does not encircle the residual limb.

2. A socket as in claim 1, wherein the flexible member does not extend underneath the distal end of the residual limb.

3. A socket as in claim 1, wherein the flexible member is a patch of flexible fabric.

4. A socket as in claim 1, wherein the hard wall of the socket comprises no patellar bar for pressing against the wearer's patellar tendon.

5. An external below-the-knee prosthesis socket comprising: a socket hard wall surrounding and defining a socket interior space and having an upper edge defining an opening for receiving a residual limb of a wearer into the socket interior space; wherein said socket hard wall comprises a V-shaped notch in said upper edge, wherein the notch extends downwardly to provide a gap in the hard wall adapted to be located where a wearer's patellar tendon will reside when the residual limb is in the socket interior space; and a flexible member provided in said V-shaped notch and connected to said socket hard wall so that the flexible member extends across the notch for contacting the wearer's residual limb or liner-covered residual limb, wherein the flexible member is glued to the hard socket.

6. An external below-the-knee prosthesis socket comprising: a socket hard wall surrounding and defining a socket interior space and having an upper edge defining an opening for receiving a residual limb of a wearer into the socket interior space; wherein said socket hard wall comprises a V-shaped notch in said upper edge, wherein the notch extends downwardly to provide a gap in the hard wall adapted to be located where a wearer's patellar tendon will reside when the residual limb is in the socket interior space; and a flexible member provided in said V-shaped notch and connected to said socket hard wall so that the flexible member extends across the notch for contacting the wearer's residual limb or liner-covered residual limb, wherein the hard wall comprises two recesses that extend inward into the interior space of the socket on each of two sides of said V-shaped notch, for pressing against the wearer's anterior tibial condyle.

7. An external below-the-knee prosthesis socket comprising: a rigid socket wall surrounding and defining a socket interior space and having a top edge defining an opening for receiving a residual limb of a wearer into the socket interior space; wherein the top edge has an uppermost portion and a lowermost edge portion and said lowermost portion is a V-shaped notch that extends generally vertically downward a distance of 4-6 inches below said uppermost portion of the top edge, wherein said notch provides a gap in the rigid socket wall that is adapted to be located where a wearer's patellar tendon will reside when the residual limb is in the socket interior space; and a non-rigid member provided in said V-shaped notch and connected to said rigid wall so that the non-rigid member extends across said gap for contacting the wearer's residual limb or liner-covered residual limb, and wherein said non-rigid member does not extend upward as high as said uppermost portion of the top edge.

8. A socket as in claim 7, wherein the non-rigid member does not encircle the residual limb.

9. A socket as in claim 7, wherein the non-rigid member does not extend underneath the distal end of the residual limb 10. A socket as in claim 7, wherein the non-rigid member is glued to the hard socket.

11. A socket as in claim 7, wherein the non-rigid member is a patch selected from the group consisting of: fabric, rubber, and leather.

12. A socket as in claim 7, wherein the rigid socket wall has an interior surface that further comprises two convex portions that protrude into the socket interior space on each of two sides of said V-shaped notch, for pressing against the wearer's anterior tibial condyle.

13. A socket as in claim 7 wherein the rigid socket wall comprises no patellar bar for pressing against the wearer's patellar tendon.

14. A method of making a below-the-knee prosthesis socket, the method comprising: forming a hard socket wall having a top edge, the top edge having a V-shaped notch extending axially downward to provide a gap in the socket wall into which a wearer's patellar tendon resides when the wearer's residual limb is in said socket; so that no portion of the hard socket wall presses against the patellar tendon during use of the socket, further comprising forming indentations in the hard socket wall on each of two sides of the V-shaped notch, wherein said indentations protrude into the interior space of the socket to press against the wearer's anterior tibial condyle.

15. A method of claim 14, further comprising providing a flexible patch across the V-shaped notch and generally parallel to the hard socket wall, so that said flexible patch contacts the wearer's liner-covered residual limb at the patellar tendon.

16. A method of claim 14, wherein said socket comprises no patellar tendon bar.

17. A method of claim 14, wherein said socket comprises no horizontal ledge in the interior surface of the hard socket wall at the patellar tendon region of the residual limb.

* * * * *